(12) United States Patent
Barker, Jr. et al.

(10) Patent No.: US 8,641,662 B2
(45) Date of Patent: Feb. 4, 2014

(54) SYSTEMS, DEVICES, METHODS FOR DELIVERING HYDROGEL COMPOSITIONS WITH SELF-PURGING TO PREVENT CLOGGING

(75) Inventors: Peter Barker, Jr., Bonsall, CA (US); William Jerome Mezger, Trabuco Canyon, CA (US)

(73) Assignee: Neomend, Inc., Irvine, CA (US)

( * ) Notice: Subject to any disclaimer, the term of this patent is extended or adjusted under 35 U.S.C. 154(b) by 484 days.

(21) Appl. No.: 13/080,054

(22) Filed: Apr. 5, 2011

(65) Prior Publication Data

US 2011/0245803 A1 Oct. 6, 2011

Related U.S. Application Data

(60) Provisional application No. 61/320,909, filed on Apr. 5, 2010.

(51) Int. Cl.
*A61M 37/00* (2006.01)
*A61M 31/00* (2006.01)
(52) U.S. Cl.
USPC ............................................ 604/82; 604/518
(58) Field of Classification Search
USPC ........... 604/500, 514, 518, 57, 82, 83, 84, 85, 604/89, 141, 246, 247, 266, 269
See application file for complete search history.

(56) References Cited

U.S. PATENT DOCUMENTS

| | | | |
|---|---|---|---|
| 5,887,755 A * | 3/1999 | Hood, III | 222/135 |
| 6,371,975 B2 | 4/2002 | Cruise et al. | |
| 6,458,147 B1 | 10/2002 | Cruise et al. | |
| 6,562,059 B2 | 5/2003 | Edwards et al. | |
| 6,673,093 B1 * | 1/2004 | Sawhney | 606/214 |
| 6,733,515 B1 | 5/2004 | Edwards et al. | |
| 6,743,248 B2 | 6/2004 | Edwards et al. | |
| 6,830,756 B2 * | 12/2004 | Hnojewyj | 424/426 |
| 6,994,686 B2 * | 2/2006 | Cruise et al. | 604/82 |
| 8,377,507 B2 * | 2/2013 | Wawrzyniak et al. | 427/207.1 |
| 2003/0209612 A1 | 11/2003 | Hahnen | |
| 2009/0076459 A1 * | 3/2009 | Goldberg | 604/191 |
| 2010/0217231 A1 * | 8/2010 | Ilan et al. | 604/506 |
| 2011/0245866 A1 * | 10/2011 | Cassingham et al. | 606/213 |

OTHER PUBLICATIONS

International Search Report and Written Opinion for PCT/US2011/031192 dated Dec. 27, 2011.

* cited by examiner

*Primary Examiner* — Emily Schmidt
*Assistant Examiner* — Andrew Gilbert
(74) *Attorney, Agent, or Firm* — Pepper Hamilton LLP

(57) ABSTRACT

A hydrogel composition is formed by conveying separate first and second liquid components subject to a selectively applied application pressure P(A) into an outlet path for mixing and discharge. A liquid flushing agent is automatically conveyed into the outlet path subject to a substantially constantly applied purge pressure P(P) when the application of P(A) is interrupted, to continuously flush residual hydrogel composition from the outlet path.

10 Claims, 4 Drawing Sheets

SYSTEMS, DEVICES, METHODS FOR DELIVERING HYDROGEL COMPOSITIONS WITH SELF-PURGING TO PREVENT CLOGGING

CROSS-REFERENCE TO RELATED APPLICATIONS

This application claims benefit to and priority of U.S. Provisional Patent Application No. 61/320,909 filed on Apr. 5, 2010 entitled "Systems, Devices, Methods For Delivering Hydrogel Compositions With Self-Purging To Prevent Clogging," the entire contents of which are hereby incorporated by reference.

FIELD OF THE INVENTION

The invention generally relates to systems, devices, and methods for applying compositions of materials that polymerize or cross-link at the instance of use, and, in particular, that apply compositions of this type in the medical field.

BACKGROUND OF THE INVENTION

Systems, devices, and methods for applying compositions of materials that polymerize or cross-link at the instance of use typically consist of an applicator that brings together two liquid components (e.g., albumin and PEG) into a spray tip. Within the spray tip, the liquid components mix and begin a rapid polymerization process to form a hydrogel. As long as the operator maintains the continuous flow of the two components into and through the spray tip, the spray tip will not clog up. However, as soon as the operator stops the flow of the components, a residual amount of the components remains within the spray tip and continues to polymerize into a solid hydrogel, and thus clog the spray tip.

Conventional spray tip devices include a port for pressurized air to be directed through the spray tip, to prevent the hydrogel from clogging within the spray tip. However, this device is cumbersome and requires accessories such as tubing, a pressure regulator, and a pressurized air source.

SUMMARY OF THE INVENTION

The invention provides systems, devices, and methods that systematically remove undischarged, residual mixtures of first and second liquid components from an outlet path of an applicator.

One aspect of the invention provides self-purging systems and methods for delivering a hydrogel material formed by mixing first and second liquid components. The systems and methods comprise an applicator sized and configured to mix the first and second liquid components and form the hydrogel composition. The applicator includes separate inlet paths that separately convey the first and second liquid components subject to a selectively applied application pressure P(A) into a single outlet path for mixing and formation of the hydrogel composition for discharge from the single outlet path.

The systems and methods also include a purge assembly comprising a source of liquid flushing agent subject to a substantially constantly applied purge pressure P(P), which is maintained at a magnitude that is less than P(A). The purge assembly further includes a purging path coupling the source to the single outlet path of the applicator to convey liquid flushing agent into single the outlet path subject to the substantially constantly applied purge pressure P(P).

The purge assembly includes a valve assembly communicating with the purging path and the single outlet path. The valve assembly is operable in response to localized pressure conditions between first and second flow conditions.

The first flow condition permits the flow and mixing of the first and second liquid components but not the liquid flushing agent in the single outlet path subject to the application of P(A), for dispensing the hydrogel composition from the single outlet path.

The second flow condition permits the flow of liquid flushing agent but not the first and second liquid components in the single outlet path subject to the substantially constantly applied purge pressure P(P), to continuously flush residual hydrogel composition from the single outlet path.

The valve assembly is automatically placed in the first flow condition in response to localized pressure conditions whenever P(A) is applied and is automatically placed in the second flow condition in response to localized pressure conditions during an interruption of the application of P(A).

Features and advantages of the inventions are set forth in the following Description and Drawings, as well as in the appended Claims.

BRIEF DESCRIPTION OF THE DRAWINGS

FIG. 1 is an exploded perspective view of a system delivering a hydrogel composition with a self-purging assembly.

FIG. 2 is an assembled perspective view of the system shown in FIG. 1.

FIG. 3 is a perspective view of the system shown in FIG. 2 in use, with the purge assembly in a first flow condition permitting the flow and mixing of the first and second liquid components within an applicator to form and dispense the hydrogel composition, but not permitting the flow of a liquid flushing agent into the applicator.

FIG. 4 is a perspective view of the system shown in FIG. 2 in use, with the purge assembly in a second flow condition permitting the flow of liquid flushing agent subject to a substantially constantly applied purge pressure to continuously flush residual hydrogel composition from the applicator.

DESCRIPTION OF PREFERRED EMBODIMENTS

This detailed description is meant to be illustrative only and is not meant to limit the invention. For example, a dual barrel syringe system is disclosed. Three barrel systems, or other systems and arrangements may also be used.

FIGS. 1 and 2 show a system 10 for delivering a material that is formed from two or more liquid components 12 and 14, which are mixed at the instance of use. When mixed, the liquid components begin a rapid polymerization process to form a hydrogel composition 16, as FIG. 3 shows.

The components 12 and 14 can vary. For example, the first component 12 can comprise a liquid material having one or more nucleophilic (electron donator) groups. The second component 14 can comprise a liquid material having one or more electrophilic (electrode withdrawing) groups. As FIG. 3 shows, the formative components 12 and 14, upon mixing, cross-link, transforming from a liquid state to a biocompatible hydrogel composition 16 (in a process called "gelation").

After gelation, the hydrogel composition 16 exhibits desired mechanical properties that can include adhesive strength, cohesive strength, and elasticity. In a representative embodiment, the hydrogel composition 16 is intended for use in the medical field. In this arrangement, depending upon its mechanical properties, the hydrogel composition 16 can be used, e.g., as a tissue sealant, a tissue adhesion barrier, a tissue void filler, or a carrier for a therapeutic agent.

In one representative example, the nucleophilic first component 12 can comprise a protein solution (e.g., albumin) and the second electrophilic component 14 can comprise a polymer (e.g., poly(ethylene glycol) or PEG).

Figure 1:
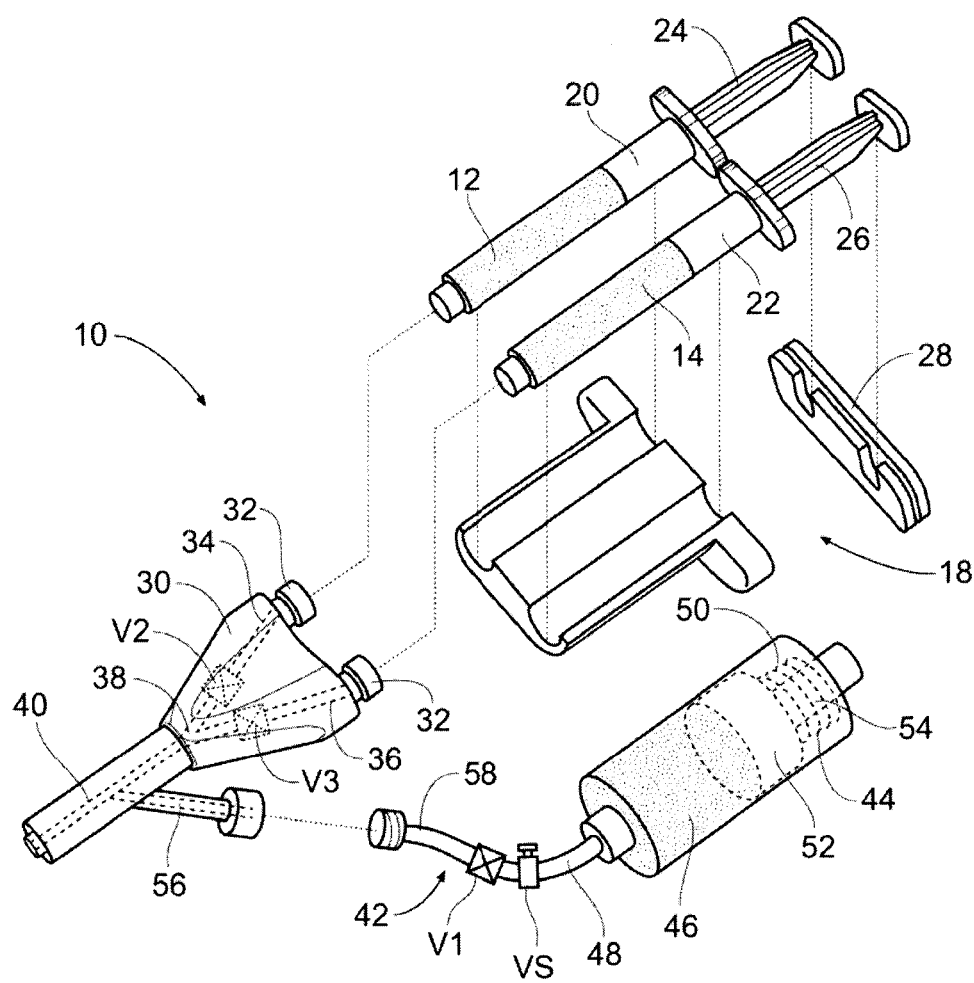
Figure 2:
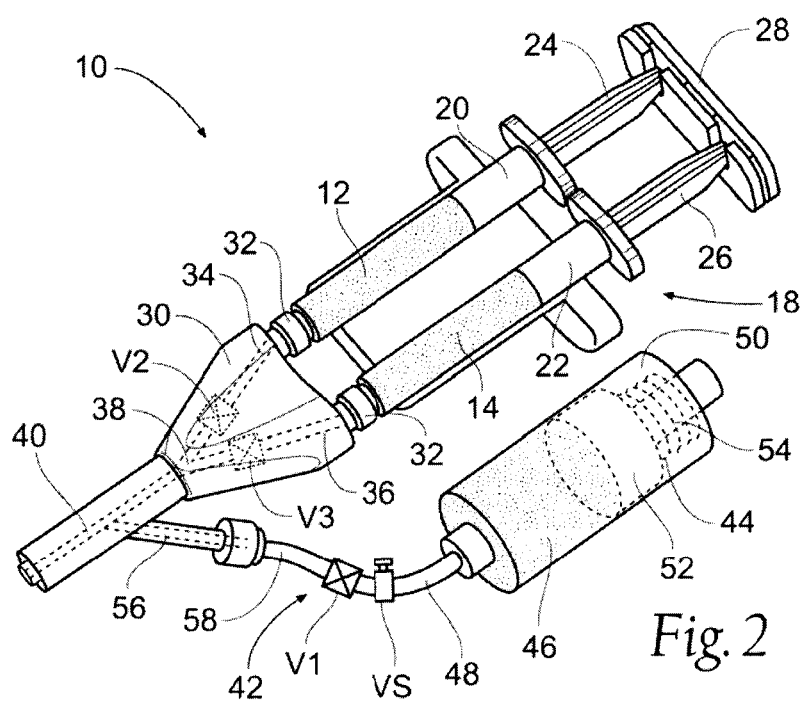

The delivery system 10 includes a dual syringe assembly 18. The dual syringe assembly 18 can be conventional in construction and is shown in FIGS. 1 and 2 for illustration purposes only. The dual syringe assembly 18 includes a pair of side-by-side syringe barrels 20 and 22. One barrel 20 is sized and configured to receive the first liquid component 12, and the other barrel 22 is sized and configured to receive the second liquid component 14. A syringe piston 24 and 26 is advanceable within each syringe barrel 20 and 22, respectively, to dispense the respective component 12 and 14 from the dispensing end of the respective barrel 20 and 22.

The syringe pistons 24 and 26 are joined by a clip 28. The syringe clip 28 mechanically links the syringe pistons 24 and 26 together for common advancement inside their respective syringe barrels 20 and 22. The operator is thereby able to hold and operate dual syringe barrels 20 and 22 in the same way as a single syringe barrel.

The system 10 includes an applicator 30. The applicator 30 includes at one end a pair of luer-type fittings 32 that couple to the dispensing ends of the syringe barrels 20 and 22.

The applicator 30 includes interior channels 34 and 36 coupled to the luer fittings 32. The channels 34 and 36 merge at a Y-junction 38 into a single outlet path 40. The applicator 30 maintains two liquid components 12 and 14 dispensed by the dual syringe barrels 20 and 22 separate until they reach the Y-junction 38. The clip 28 ensures even application of individual components 12 and 14 through the applicator at a given application pressure P(A).

At the Y-junction 38 and then through the outlet path 40, the two components 12 and 14 mix and cross-link while flowing subject to the application pressure P(A) in the liquid state, in a process that will, in shorthand, be called "channel-mixing." During channel mixing, gelation begins to form the hydrogel composition 16 as it is dispensed from outlet path 40. The outlet path 40 can be sized and configured, e.g., to serve as a spray tip for discharging the gelating hydrogel composition as a spray into contact with tissue.

The parts of the dual syringe assembly 18 and applicator 30 can be made, e.g., by molding medical grade plastic materials, such as polycarbonate and acrylic.

Termination of the application pressure P(A) by operation of the dual syringe assembly 18 can leave undischarged, residual mixtures of the first and second components 12 and 14 within the outlet path 40. The residual mixtures can undergo further gelation within the outlet path 40 to form the hydrogel composition 16. Presence of the hydrogel composition 16 within the outlet path 40 can clog or impede the subsequent passage of liquids through the outlet path 40.

To systematically remove undischarged, residual mixtures of the first and second components 12 and 14 from the outlet path 40, the system 10 includes a purging assembly 42 coupled to the applicator 30. The purging assembly 42 includes a source 44 of a liquid flushing agent 46, e.g., water, and when used in the medical field, sterile water. The purging assembly 42 also includes a purging path 48 that leads from the source 44 to the outlet path 40 of the applicator 30. The purging path 48 communicates with the outlet path 30.

The source 44 is subject to an applied preselected purging pressure P(P). The purging pressure P(P) is continuously applied and is selected to be less than the application pressure P(A), for reasons that will be described later.

The purging pressure P(P) normally urges the liquid flushing agent 46 from the source 44 through the purging path 48 toward the outlet path 40.

Within the outlet path 40, the liquid flushing agent 46 discharges residual mixtures of the first and second components 12 and 14 from the outlet path 40 at the purging pressure P(P), before gelation of the hydrogel composition substantially occurs. Clogging of the outlet path 40 is thereby prevented or moderated.

The purging assembly includes a first valve V1 in the purging path 48 between the source 44 and the outlet path 40 of the applicator 30. The valve V1 operates in response to localized pressure conditions within the purging path 48 between a closed condition and an opened condition. In the closed condition, the valve V1 prevents the pressurized flow of the liquid flushing agent 46 through the purging path 48. In the opened condition, the valve V1 allows the pressured flow of the liquid flushing agent 46 through the purging path 48. The valve V1 is sized and configured to assume the closed condition when pressure conditions in the purging path 48 downstream of the valve V1 (i.e., toward the outlet path 40) exceed the pressure conditions in the purging path 48 upstream of the valve V1 (i.e., toward the source 44).

The applicator 30 includes a second valve V2 in the channel 34 and a third valve V3 in the channel 36 in an upstream flow direction from the Y-junction 38. Each valve V2 and V3 operates in response to localized pressure conditions within the respective channels 34 and 36 between a closed condition and an opened condition. In the closed condition, each valve V2 and V3 prevents the back flow of liquid through the respective channel 34 and 36 from the Y-junction 38 toward the syringe assembly 18. In the opened condition, each valve V2 and V3 allows the flow of liquid through the respective channel 34 and 36 toward the Y-junction 38. Each valve V2 and V3 is sized and configured to assume the closed condition when pressure conditions upstream of the valve V2 and V3 in the respective channel 34 and 36 (i.e., toward the syringe assembly 18) are less than the pressure conditions in the channels 34 and 36 downstream of the valves V2 and V3 (i.e., toward the Y-junction 38 and outlet 40).

Figure 3:
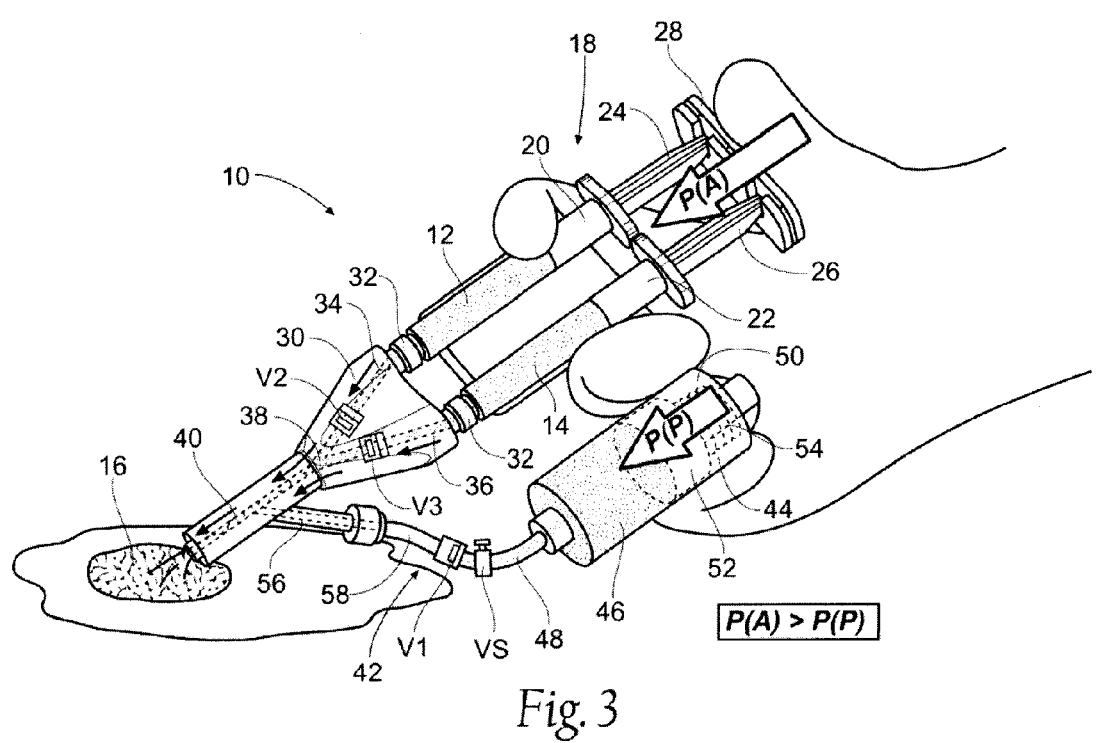

By selecting the purging pressure P(P) to be less than the application pressure P(A) (as above described), the valve V1 will occupy the closed condition and the valves V2 and V3 will occupy the opened condition whenever the dual syringe assembly 18 is operated to apply the application pressure P(A), as FIG. 3 shows, comprising a first flow condition. In the first flow condition, during the application of the pressure P(A), the two liquid components 12 and 14 enter the channels 34 and 36 of the applicator 30, flow through the open valves V2 and V3 to converge at the Y-junction 38, and proceed through the outlet path 40, undergoing channel-mixing. In the first flow condition, during the application of the pressure P(A), the forming hydrogel composition 16 is dispensed from the outlet path 40. In the first flow condition, the valve V1 is in the closed condition—because P(A) exceeds P(P)—and the liquid flushing agent 46 is prevented from flowing from the source 44 into the outlet path 40.

Figure 4:
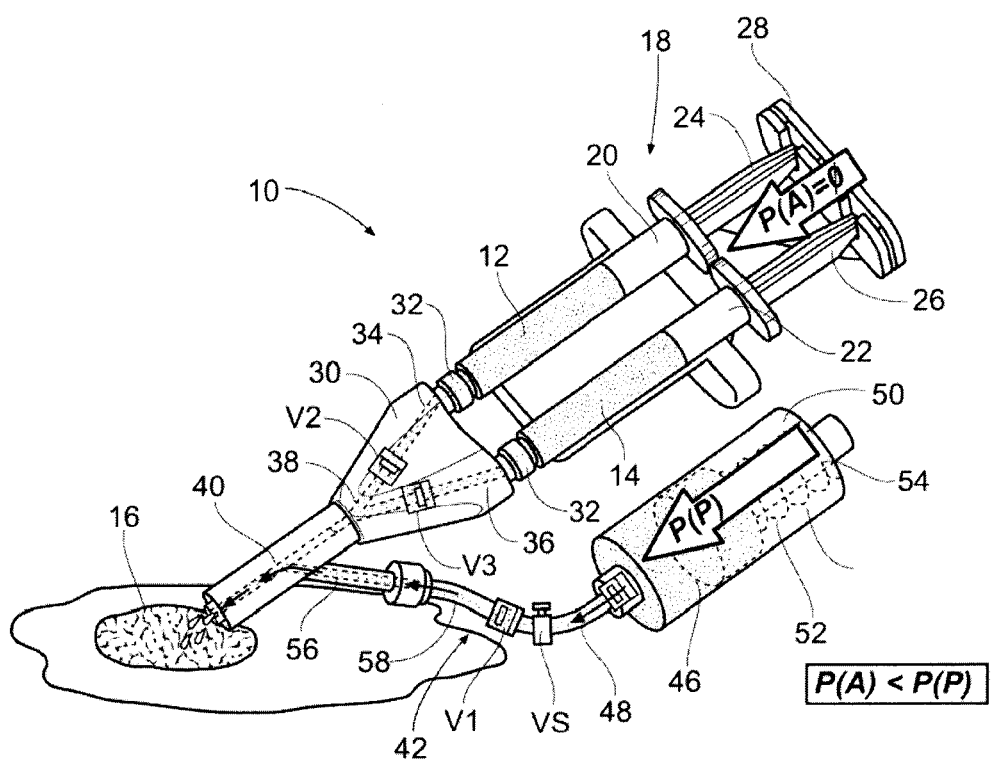

When the application pressure P(A) is removed, e.g., when the operator seeks to interrupt the discharge of the forming hydrogel composition 16 from outlet path 40, the pressure conditions at the valves V1, V2, and V3 change, as FIG. 4 shows, comprising a second flow condition. In the second flow condition, the pressure condition upstream of the valve V1 (i.e., the constantly applied preselected purging pressure P(P)) exceeds the pressure conditions downstream of the valve V1 (because the application pressure P(A) is no longer being applied).

As FIG. 4 shows, the valve V1 assumes the opened condition, and the valves V2 and V3 assume the closed condition, to thereby allow the pressured flow of the liquid flushing agent 46 (in some embodiments, a gas flushing agent can be employed) through the purging path 48 and into and through the outlet path 40. The liquid flushing agent 46 discharges residual mixtures of the first and second components 12 and 14 from the outlet path 40 at the purging pressure P(P).

Because the purging pressure P(P) is constantly applied, the flow of the liquid flushing agent into the outlet path 40 occurs substantially simultaneously with the cessation of the application pressure P(A). Therefore, the residual mixtures of the first and second components 12 and 14 are discharged from the outlet path 40 by the flow of the liquid flushing agent 46 before gelation of the hydrogel composition can substantially occur. Clogging of the outlet path 40 is thereby prevented or moderated.

Thus, the assembly of valves V1, V2, and V3 is automatically placed in the first flow condition in response to localized pressure conditions whenever P(A) is applied, and conversely, the assembly of valves V1, V2, and V3 is automatically placed in the second flow condition in response to localized pressure conditions immediately when an interruption of the application of P(A) occurs.

The purging assembly 42 can be various arranged and constructed. As shown in FIGS. 1 and 2, the source 44 of the liquid flushing agent comprises a canister barrel 50 including a piston 52 that is biased by a spring 54 to advance within the canister barrel 50.

In this arrangement, the purging path 48 includes a conduit that leads from an outlet of the canister barrel 50 into the outlet path 40 of the applicator 30. In the illustrated embodiment, the purging path 48 includes a molded fitting 56 defining a lumen on the applicator 30, and a length of flexible tubing 58 coupled at one end to the fitting 56 (by a disconnecting luer lock) and at the other end to the outlet of the canister 50 (which can include a disconnecting luer lock as well). In an alternate embodiment, the canister 50 and purging path 48 can comprise integrally attached components of the applicator 30. In this arrangement, the valve V1 can include a conventional one-way check valve assembly that closes when pressure conditions downstream of the valve V1 exceed the pressure conditions upstream of the valve V1, to prevent a backflow of fluid through the valve V1, but that is otherwise open to allow a forward flow of fluid through the valve V1. Likewise, the valves V2 and V3 can comprise conventional one-way check valves.

In the illustrated embodiment, a manually operated safety valve VS is provided upstream of the one-way check valve V1, to selectively toggle the purging assembly 42 between an inactivated condition (by closing the safety valve VS) and an activated condition (by opening the safety valve VS). When in the activated condition, the constantly applied purging pressure P(P) provides a steady drip of liquid flushing agent 46 into the outlet path 40 in the absence of application pressure P(A) applied by the operator using the dual syringe assembly 18. The constant drip actively clears the outlet path 40 whenever the dual syringe assembly 18 is not in use.

Alternate embodiments include the use of a pneumatic pressurized canister of water to allow the constant drip. This embodiment replaces the use of a spring activated piston.

Another alternative embodiment allows the water canister to be housed away from the applicator itself. In this arrangement, the water canister can comprise a separate component, sized and configured, e.g., to placed on or alongside the patient, coupled by flexible tubing to the applicator. This allows the dual syringe assembly and applicator to be smaller and lighter for ease of use.

Another alternate embodiment includes using a different flushing agent besides water. A flushing agent that will slow gelation time can allow for better clearing of faster gelling compositions from the outlet path.

Another alternate embodiment allows, through selective operation of a safety valve, a sudden, short purge of water through the nozzle to provide nozzle clearing. Instead of the constant purge, this embodiment may reduce the amount of water needed and decrease the size of the overall system. In some embodiments, the sudden, short purge can be achieved through subsequent operation of a flush trigger or button. In some embodiments, the sudden, short burst of flushing agent is automatically generated when the syringe plunger stops moving forward. An actuator can sense the lack of movement, activate a pulsed release of flushing agent.

The features of the invention are set forth in the following claims.

We claim:

1. A self-purging system for delivering a hydrogel composition formed by mixing first and second liquid components comprising, an applicator sized and configured to mix the first and second liquid components and form the hydrogel composition, the applicator including inlet paths that convey the first and second liquid components subject to a selectively applied application pressure P(A) into an outlet path for mixing and formation of the hydrogel composition for discharge from the outlet path, and a purge assembly comprising a source of liquid flushing agent subject to a substantially constantly applied purge pressure P(P) that is maintained at a magnitude that is less than P(A), and a purging path coupling the source to the outlet path to convey liquid flushing agent into the outlet path subject to the substantially constantly applied purge pressure P(P), the purge assembly further including a valve assembly communicating with the purging path and the outlet path being operable in response to localized pressure conditions in first and second flow conditions, the first flow condition permitting the flow and mixing of the first and second liquid components but not the liquid flushing agent in the outlet path during the application of P(A), for dispensing the hydrogel composition from the outlet path, the second flow condition permitting the flow of liquid flushing agent but not the first and second liquid components in the outlet path subject to the substantially constantly applied purge pressure P(P), for continuously flushing residual hydrogel composition from the outlet path, the valve assembly being automatically placed in the first flow condition in response to localized pressure conditions whenever P(A) is applied, the valve assembly being automatically placed in the second flow condition in response to localized pressure conditions during an interruption of the application of P(A).

2. A system according to claim 1, wherein the valve assembly includes a first valve element between the source and the outlet path operable in response to localized pressure conditions within the purging path between a closed condition and an opened condition, in the closed condition, the first valve element preventing pressurized flow of the liquid flushing agent through the purging path, in the opened condition, the first valve element allowing pressured flow of the liquid flushing agent through the purging path, the first valve element being sized and configured to assume the closed condition when pressure conditions in the purging path downstream of the first valve element exceed the pressure conditions in the purging path upstream of the first valve element.

3. A system according to claim 2,
wherein the valve assembly includes second and third valve elements in the inlet paths of the applicator upstream of the outlet path, each second and third valve element operating in response to localized pressure conditions within the respective inlet path between a closed condition and an opened condition, in the closed condition, each second and third valve element preventing the flow of liquid through the respective inlet path away from the outlet path, in the opened condition, each second and third valve element allowing the flow of liquid through the respective inlet path toward the outlet path, each second and third valve element being sized and configured to assume the closed condition when pressure conditions upstream of the second and third valve elements are less than the pressure conditions in the respective inlet path downstream of the second and third valve elements.

4. A system according to claim 1,
wherein the valve assembly includes a first one-way valve element in the purging path downstream of the source, and second and third one-way valve elements in the inlet paths for the first liquid component and second liquid component, respectively, upstream of the outlet path.

5. A system according to claim 1,
wherein the purge assembly includes a manually operable control element to selectively enable and disable operation of the purge assembly.

6. A system according to claim 5,
wherein the control element includes a valve in the purging path manually operable between a closed condition disabling operation of the purge assembly and an opened condition enabling operation of the purge assembly.

7. A system according to claim 1,
wherein the source comprises a vessel, and wherein the substantially constantly applied purge pressure P(P) comprises operation of a spring biased piston within the vessel.

8. A system according to claim 1,
wherein the source comprises a vessel, and wherein the substantially constantly applied purge pressure P(P) comprises pneumatic pressure within the vessel.

9. A method for delivering a hydrogel composition comprising,
forming the hydrogel composition by conveying separate first and second liquid components subject to a selectively applied application pressure P(A) into an outlet path for mixing,
discharging the hydrogel composition from the outlet path by the application of the pressure P(A), and
coupling to the outlet path a source of liquid flushing agent subject to a substantially constantly applied purge pressure P(P) that is maintained at a magnitude that is less than P(A),
establishing, in response to localized pressure conditions when P(A) is applied, a first flow condition permitting flow and mixing of the first and second liquid components in the outlet path, while simultaneously blocking the flow of the liquid flushing agent in the outlet path, for dispensing the hydrogel composition from the outlet path, and
establishing, in response to localized pressure conditions when the application of P(A) is interrupted, a second flow condition permitting the flow of the liquid flushing agent in the outlet path subject to the substantially constantly applied purge pressure P(P), while simultaneously blocking the flow of the first and second liquid components into the outlet path, to continuously flush residual hydrogel composition from the outlet path during an interruption of P(A).

10. A method according to claim 9,
further including selectively enabling or disabling the establishment of the second flow condition.

\* \* \* \* \*